United States Patent [19]
Okazaki et al.

[11] Patent Number: 5,750,150
[45] Date of Patent: May 12, 1998

[54] COMPOSITIONS FOR TREATING AFFECTED TISSUES, METHOD FOR THE PREPARATION AND USAGE THEREOF

[75] Inventors: Hideo Okazaki, Tokyo; Kinuko Oku, Naha, both of Japan

[73] Assignee: Traditional Chinese Medicine Research Laboratory, Inc., Naha, Japan

[21] Appl. No.: 652,648

[22] Filed: May 28, 1996

Related U.S. Application Data

[63] Continuation-in-part of Ser. No. 411,704, May 15, 1995, abandoned, and Ser. No. 424,523, PCT/JP93/01347 filed Sep. 20, 1993, PCT/JP94/01942 filed Nov. 17, 1994, abandoned.

[30] Foreign Application Priority Data

| Sep. 18, 1992 | [JP] | Japan | 4-275132 |
| Nov. 17, 1993 | [JP] | Japan | 5-288323 |
| Jul. 22, 1994 | [JP] | Japan | 6-192219 |

[51] Int. Cl.$^6$ .......... A61K 33/04; A61K 33/06; A61K 33/10; A61K 31/70

[52] U.S. Cl. .......... 424/682; 424/685; 424/711; 514/23; 514/25; 514/574; 514/882

[58] Field of Search .......... 424/682, 685, 424/711; 514/23, 25, 882, 574

[56] References Cited

U.S. PATENT DOCUMENTS 5,252,344  10/1993  Shi .......... 424/682

FOREIGN PATENT DOCUMENTS

| 4-225920 | 8/1992 | Japan . |
| 94-06443 | 3/1994 | WIPO . |

OTHER PUBLICATIONS

"Aluminum Potassium Sulfate", Commentary on Pharmacopedia Japonica, 12th Revision, 1991, pp. D–1019–1021, with translation.

Yuan, et al., "Experimental Study of Xiaozhiling injection", Journal of Traditional Chinese Medicine, vol. 1, No. 2, 1981, pp. 87 and 116.

*Primary Examiner*—Phyllis G. Spivack
*Attorney, Agent, or Firm*—Foley & Lardner

[57] ABSTRACT

Injectable compositions for treating affected tissues are prepared by formulating sodium hydrogen sulfite with all other components except tannic acid to yield a first mixture and adding tannic acid to the first mixture, or, by formulating a water-soluble aluminum compound and a chelating agent to yield a first formulation, formulating tannic acid and sodium hydrogen sulfite to yield a second formulation and admixing the first formulation with the second formulation to yield a second mixture and, as needed, adding a polyvalent alcohol and/or a saccharide to the first and/or second formulations or to the first or second mixture, thereby formulating the injectable composition having a pH range of from pH 1.0 to pH 3.5. This preparation can prevent the oxidation of tannic acid and the direct reaction with aluminum ions derived from sodium hydrogen sulfite, whereby the composition can provide a stable formulation as well as ensure effectiveness as an injectable preparation in a solution form.

34 Claims, No Drawings

COMPOSITIONS FOR TREATING AFFECTED TISSUES, METHOD FOR THE PREPARATION AND USAGE THEREOF

This is a continuation in part of U.S. Ser. No. 08/411,704 filed May 15, 1995, abandoned, which is the national stage application of PCT/JP93/01347 filed Sep. 20, 1993, and U.S. Ser. No. 08/424,523 filed May 26, 1995, abandoned, which is the national stage application of PCT/JP94/01942 filed Nov. 17, 1994.

BACKGROUND OF THE INVENTION

1. Field of the Invention

The present invention relates to a composition for treating affected tissues, a method for the preparation thereof, and usage thereof and, more particularly, to a stable composition for treating affected tissues of the digestive system caused, for example, by piles or hemorrhoids, brain aneurysm, hepatic tumor vessels, and the like, a method for the preparation of the composition therefor, and usage thereof for treating such affected tissues.

2. Description of the Related Art

Injection therapy for treating and curing internal piles or hemorrhoids has a history of more than 100 years. The early injections used for the such therapy were composed of a ferrous sulfate solution, phenol in olive oil, and the like. Thereafter, there were used an alcohol, quinine hydrochloride, mercuric chloride, urethan, ergot and the like. In the past thirty years, a phenol solution in vegetable oil and an alum solution have been used most frequently for treating and curing the internal piles or hemorrhoids.

These compositions, however, cannot be said to satisfactorily solve all or most of such problems for treating and curing internal piles or hemorrhoids for reasons as will be described hereinafter. It is noted that the injection therapy for sclerosing the internal piles or hemorrhoids requires for the injectable preparations to reduce inflammation, to stop bleeding, to inhibit the growth of bacteria, to bring about well-formed thrombosis and to complete fibrosis of hemorrhoidal blood vessels without leaving any hard nodules or causing necrosis. The injectable preparations so far developed for treating and curing the internal piles or hemorrhoids by sclerosing the affected abnormal tissues of the digestive system, however, do not satisfy any or a majority of the requirements as described immediately hereinabove. It is also noted as difficult to determine the appropriate concentration and quantity of the injectable preparations used at clinical needs, as well as a procedure to sclerose the internal piles or hemorrhoids without causing necrosis. It is further required that the methods of injection therapy and administration be improved so as to expand the area to be injected because the composition be deposited only in the submucosa when injected.

As a composition for treating and curing internal piles or hemorrhoids, there is proposed an injectable agent that comprises tannin, alum, sodium citrate, dextran glycerin and trichlorobutyl alcohol (Journal of Traditional Chinese Medicine: vol. 1, No. 2, pp. 116–120 (1981)). Alum can be referred to as aluminum potassium sulfate and it is a colorless and transparent substance of an octahedral crystal. It has locally astringent, hemostatic and antiseptic properties. Alum is not absorbed through the gastroenteric mucosa when administered internally and exerts merely a local action against the mucosa. On the other hand, tannic acid is usually obtained from nutgall or gall and may be a yellow-white or pale brown, amorphous and powdery substance or a small-leaf-shaped or spongy bulky substance. Tannic acid can cause a protein to coagulate in an acidic or neutral solution and has astringent, antiseptic and antibacterial properties.

It is further noted that aluminum potassium sulfate is not allowed to be clinically used in combination with tannic acid or tannin agents (*Pharmacopedia Japonica*, The 12th Revision (1991); pp. D-1019–1021). In addition, it is also known that tannic acid forms a less soluble salt with basic organic chemical substances and a non-soluble or sparingly soluble compound with an iron agent or the like, thereby losing its effects.

The injectable preparations as described immediately hereinabove contains trichlorobutyl alcohol so that there is the possibility that it presents the problems as will be described hereinafter. It is known that trichlorobutyl alcohol is a compound in which carbon atoms and chlorine atoms are combined with each other and it can oxidize tannic acid due to the formation of a radical upon the absorption of light, thereby causing tannic acid to turn into precipitated materials having a brown or black color. Further, trichlorobutyl alcohol has the property that the linkage between the carbon and chlorine atoms is broken upon application of high energy such as heat or light, turning into unstable substances. It is thus said to be inappropriate to use trichlorobutyl alcohol as a component of a medicine due to its such property because there is the highly probable risk that it causes precipitates in the injectable preparations during storage. In addition, the use of such a compound is less convenient in handling and storing because the greatest possible care is required for storing the injectable preparations containing it.

Further, Japanese Patent Unexamined Publication Kokai No. 4-225,920 discloses an agent for hardening or sclerosing the affected abnormal tissues of the digestive system such as, for example, esophagophlebangioma, piles or hemorrhoids, rectal prolapse, prolapse of the rectal mucosa and the affected uplift tissues of the large intestine and the rectum. The sclerosing agent consists of a composition comprising tannic acid, aluminum potassium sulfate and a stabilizing agent including an extract of a medicinal plant, containing a phenol, a flavone or a flavonoid, a catechin or a polycarboxylic acid. As this composition contains the extract of the medicinal plant as the stabilizing agent, however, it suffers from the disadvantages in terms of formulating preparations that it is extremely difficult to provide injectable preparations with a constant formulation and stable quality as well as that there is still the possibility that the stabilizing agent may be contaminated with minute amounts of unidentified substances even if it would be extracted and purified elaborately through plural steps. It has further been found that such a composition comprising tannic acid and aluminum potassium sulfate may cause coloring or, in some cases, precipitating, even if it contains the extract of the plant as a stabilizing agent, when stored for a long period of time in a liquid state. This also may cause the problem when it is applied as an injectable agent.

In addition, PCT International Publication No. WO94/06443 (International Publication Date: Mar. 31, 1994) of PCT International Application No. PCT/JP93/01347, filed Sep. 20, 1993, discloses a composition for curing affected abnormal tissues of the digestive system as injectable preparations, which comprises a composition containing a water-soluble aluminum compound in a concentration ranging from 0.01 mole to 0.5 mole, tannic acid at a rate of 0.5% to 25.0% with respect to the amount of the water-soluble aluminum compound, sodium hydrogen sulfite, and a polyvalent alcohol or a saccharide; in which a pH of said composition is adjusted so as to become in the range of from pH 1.5 to pH 3.5. The components of the compositions disclosed in this publication are the same as those of the ones to which the present invention is directed. This publication, however, discloses a method for the preparation of the composition for curing the affected abnormal tissues of the digestive system as well as the compositions consisting of the same components as those of the present invention. The published method comprises formulating all the components of the composition in a simultaneous way or in a random way. More specifically, the method for the preparation of the hardening or sclerosing agent disclosed in this publication comprises placing all the components in a test tube, pouring a predetermined amount of injectable distilled water for injection use with stirring in the test tube, and dissolving them to give an aqueoussolution. The resulting aqueous solution is then filled in a container such as a glass bottle, followed by removal of oxygen dissolved in the solution and replenishment of air with nitrogen gases. Thereafter, the solution is sterilized with high-pressure steam and then stored in a cold and dark place. It has been found, however, that the general method for the formulation of the composition as disclosed in this publication suffers from the extreme difficulty in preparing a stable composition with the constant formulation and that it presents the problem in the actual preparation of the compositions as an injectable agent.

Aluminum potassium sulfate, which may also be referred to as alum and is used as one component for the composition according to the present invention, has been applied as an a hemostatic agent. As described hereinabove, however, a combination of aluminum potassium sulfate with a tannic agent is prohibited to be used as medicine as set forth in *Pharmacopedia Japonica*. Nevertheless, various attempts have been made to use aluminum potassium sulfate in combination with the tannic agent as medicine; however, aluminum potassium sulfate is very unstable when it is mixed with the tannic agent as it is because it may be caused to become colored or to precipitate. Hence, the use of such an unstable composition as injectable preparations is inappropriate even in terms of safety.

Further, aluminum potassium sulfate contains a small amount of iron because it is usually prepared from bauxite as a raw material. *Pharmacopedia Japonica* regulates the acceptable contents of iron derivatives to be 20 ppm or less when aluminum potassium sulfate is employed as a raw material for medicine.

In addition, aluminum potassium sulfate may be caused to de decomposed into aluminum ions such as $Al^{3+}$, $Al(OH)^{2+}$, $Al(OH)^+$ and the like upon dissociation in a is solution and react with hydroxyl ion, OH—, to form aluminum hydroxide, $Al(OH)_3$, which are caused to precipitate in a solution. If such precipitates are formed in the solution, it is inappropriate to employ it as a composition for injectable preparations and it cannot be applied for treatment.

On the other hand, tannic acid is oxidized to form an oxide compound such as a quinone compound upon exposure to oxygen existing in air or dissolved in a solution to be used, thereby causing precipitates when the solution is used for injectable preparations. If such insoluble products are caused to precipitate in the injectable preparations, the resulting injection becomes as a matter of course inappropriate as medicine and cannot be administered.

Further, tannic acid is caused to be oxidized forming precipitates, particularly when iron ions are present in the solution. Hence, if tannic acid exists with aluminum potassium sulfate in the solution, the iron ions present in the aluminum potassium sulfate contained in the solution are reacted directly with tannic acid, leading to the formation of precipitates, and the oxidation of tannic acid is accelerated.

Furthermore, tannic acid reacts directly with aluminum ions, causing to form precipitates, if the aluminum ions are present in the solution, and it is likely to undergo oxidation.

Accordingly, a composition containing aluminum potassium sulfate and tannic acid cannot be prepared in a constant and stable manner without causing any precipitates simply by formulating all the components in a simultaneous or random way.

As the result of a detailed review on the order and conditions of formulating the components in preparing the preparations for injection, it has been found by the present inventor that the injectable preparations for curing the affected tissues having a constant and stable composition can be prepared by arranging the order of formulation of its components and the concentrations thereof. Thus, the present invention has been completed from this finding.

SUMMARY OF THE INVENTION

Therefore, the present invention has the object to provide an injectable composition in a solution form for treating and curing the affected tissues of the digestive system, for example, such as piles or hemorrhoids, brain aneurysm, hepatic tumor vessels, and the like, particularly which can solve the problems that conventional preparations for treating the affected tissues or the hardening agents for hardening the affected tissues of the digestive system, as described hereinabove, are instable during storage for a long period of time and which can sustain its stability as pharmaceutical preparations during storage for a long period of time as well as ensure effectiveness in addition to stability.

The present invention has another object to provide an injectable preparation in a solution form for treating and curing the affected tissues, which also can effectively be adapted to the affected tissues caused by, for example, piles or hemorrhoids, brain aneurysm, hepatic tumor vessels, and the like, which could not be cured by conventional pharmacotherapy.

The present invention has a further object to provide a method for the production of an injectable composition in the solution form for treating and curing the affected tissues caused by the piles or hemorrhoids, brain aneurysm, hepatic tumor vessels and the like, which causes no problems with properties as pharmaceutical preparations even during storage for a long period of time and which can ensure stability as well as effectiveness.

The present invention has a still further object to provide a use of an injectable preparation in the solution form for treating and curing the affected tissues, which can cause no problems with preparations during storage for a long period of time and which can ensure stability as well as effectiveness.

It should be noted herein that the terms "affected tissues" used herein singly unless otherwise stated are meant to include piles or hemorrhoids, brain aneurysm, hepatic tumor vessels, and the like.

In order to achieve the objects of the present invention, the injectable preparation in a solution form for treating and curing the affected tissues in accordance with the present invention may comprise at least a water-soluble aluminum compound, tannic acid, a chelating agent, and sodium hydrogen sulfite. In addition, the injectable composition in the solution form may contain a polyvalent or a saccharide as an agent for raising osmosis of the curing injectable preparation for treating and curing the affected tissues caused by, for example, piles or hemorrhoids, brain aneurysm, hepatic tumor and the like. The pH range of the injectable composition is adjusted to be from pH 1.0 to pH 3.5. The injectable preparation according to the present invention can sustain its stability as pharmaceutical preparations during storage for a long period of time as well as ensure effectiveness in addition to stability.

Further, the present invention provides a method for the preparation of the stable injectable composition in the solution form for treating affected tissues of the digestive system caused by, for example, piles or hemorrhoids, brain aneurysm, hepatic tumor and the like, when stored for a long period of time, which does not cause the tannic acid to precipitate in the composition due to avoidance of the direct reaction of the tannic acid with aluminum ions derived from the water-soluble aluminum compound. The injectable composition according to the present invention causes no problems with properties as pharmaceutical preparations even during storage for a long period of time and it can ensure stability as well as effectiveness.

In addition, the present invention provides a method of using the injectable composition in the solution form for treating the affected tissues of the digestive system caused by, for example, piles or hemorrhoids, brain aneurysm, hepatic tumor and the like.

The injectable compositions according to the present invention are suitable for treating and curing the affected tissues of the digestive system, more specifically, for treating and curing piles or hemorrhoids, brain aneurysm, hepatic tumor, and the like.

The injectable compositions according to the present invention prepared particularly by the method according to the present invention cause no precipitating during storage for a long period of time in a liquid state.

Further, the injectable compositions according to the present invention can be administered topically and in a simplified manner compared with conventional surgery therapy. They can furthermore avoid inconveniences and disadvantages as involved in surgical therapy. In addition, the injectable compositions in the solution form according to the present invention are stable during storage for a long period of time and it can ensure stability as well as effectiveness.

Other objects, features and advantages of this invention will become apparent in the course of the description that follows.

DESCRIPTION OF THE PREFERRED EMBODIMENTS

The injectable composition in the solution form for treating and curing the affected tissues of the digestive system in accordance with the present invention comprises a water-soluble aluminum compound, tannic acid, and sodium hydrogen sulfite and which has a pH range of from pH 1.0 to pH 3.5.

Further, the injectable composition according to the present invention contains a chelating agent. In addition, it may contain a polyvalent alcohol and/or a saccharide.

As the water-soluble aluminum compound to be employed for the composition for treating the affected tissues in accordance with the present invention, there may be mentioned, for example, aluminum chloride, aluminum sulfate, aluminum carbonate, aluminum acetate, aluminum nitrate, aluminum lactate, aluminum tartrate, aluminum salicylate, aluminum sodium sulfate, aluminum potassium sulfate, aluminum cesium sulfate, ammonium aluminum sulfate and the like. The water-soluble aluminum compounds may be applied singly or in combination of two or more.

In the injectable composition in the solution form according to the present invention, the water-soluble aluminum compound may be contained in concentrations ranging usually from 0.01 to 0.5 mole, preferably from 0.03 to 0.3 mole.

It is further preferred that the water-soluble aluminum compound is contained so as to amount to from approximately 1% to 10%, more preferably from approximately 2% to 5% as the effective concentrations in the injectable composition.

If the water-soluble aluminum compound would be contained in a concentration beyond the above range, the resulting injectable composition in the solution form may cause coloring or depositing during storage and it becomes inappropriate as injectable preparations and it cannot accomplish the desired effects sought to be achieved by the present invention.

The tannic acid to be employed for the injectable composition in the solution form according to the present invention may be employed one derived from a variety of plants. The most preferred one is tannic acid derived from gallnut. The tannic acid may be contained at a rate ranging usually from 0.01% to 10.0% as an effective concentration in the injectable composition. More specifically, the tannic acid may be contained at a rate ranging from 0.05% to 10.0%, preferably from 0.1% to 5.0%, as an effective concentration in the injectable composition. The rate of the tannic acid as an effective concentration in the composition may also range from 0.01% to 2.0%, preferably from 0.05% to 1.5%. The tannic acid may also be contained at a rate ranging usually from 0.01% to 2.0%, preferably from 0.05% to 1.5%, as an effective concentration in the composition. Further, the rate of the tannic acid with respect to the water-soluble aluminum compound may range usually from 0.5% to 25.0%, preferably from 1.0% to 20.0%. Although the tannic acid may be added in a concentration beyond the above range by adjusting the amounts of the other components, particularly sodium hydrogen sulfite, the resulting injectable compositions are likely to cause coloring or depositing during storage for a long period of time and they cannot accomplish the desired effects sought to be achieved by the present invention, particularly if the concentration of the tannic acid would be lesser than the amount of the water-soluble aluminum compound.

As described hereinabove, the water-soluble aluminum compound such as aluminum potassium sulfate may be decomposed to form aluminum ions such as $Al^{3+}$, $Al(OH)^{2+}$, $Al(OH)^+$ or the like, upon dissociation in the solution and react with hydroxyl ion, $OH^-$, to form aluminum hydroxide, $Al(OH)_3$. If such aluminum ions are present in the solution, tannic acid is reacted directly with them, whereby the solution is likely to cause the aluminum ions to precipitate upon direct reaction with the tannic acid.

Further, the tannic acid in a solid state is unstable against light or air and it is lesser stable in the solution from the point of view of a diffusion velocity between the reactive substances. For the purpose to prevent the oxidation of the tannic acid, there may be used an antioxidant such as, for example, sodium hydrogen sulfite. The rate of sodium hydrogen sulfite to be used as the antioxidant in accordance with the present invention may be usually from approximately 50% to 200%, preferably from approximately 70% to 150% with respect to the amount of the tannic acid. Alternatively, the sodium hydrogen sulfite may be contained at a rate ranging from 0.05% to 0.5%, preferably from 0.1% to 0.3%, as an effective concentration in the composition. If the sodium hydrogen sulfite would be contained in a concentration beyond the above range, the resulting injectable preparations cannot accomplish the desired effects sought to be achieved by the present invention.

In preparing the injectable compositions for treating the affected tissues in accordance with the present invention, the chelating agent, such as sodium citrate, is added to a solution containing the water-soluble aluminum compound before formulating tannic acid with the water-soluble aluminum compound, in order to avoid the direct reaction of the tannic acid with the water-soluble aluminum compound and to cause no coloring or precipitating. Once the chelating agent is added to the solution containing the water-soluble aluminum compound, the chelating agent is caused to react with the aluminum ions present in the solution, resulting in the formation of complex aluminum ions and removing the metal ions from the solution to which tannic acid is to be added, the metal ions being reactable with the tannic acid and as a result being likely to cause forming precipitates. To the solution treated in the manner as described hereinabove is added tannic acid to thereby yield a solution in which the tannic acid is not reacted directly with the metal ions, such as aluminum ions, derived from the water-soluble aluminum compound and in which no precipitates are formed. Theoretically, for example, if 0.65 molecule of the aluminum ion is present with respect to one molecule of sodium citrate ion and the former is to be linked to the latter, no free aluminum ion is present in the solution. Practically, however, as the sodium citrate ion exists in a neutral state or in the form of a citric acid dihydrogen ion in the range of such a strong acid as the composition according to the present invention, such amounts are insufficient to trap the aluminum ions in the 1.65-fold concentrations as complex ions. Hence, in this case, it is preferred to select a solution having the composition so as to allow free aluminum ions to exist in a range that does not exceed a solubility product constant of aluminum tannate.

As the chelating agent to be employed for the present invention, there may be mentioned any compound having the action of trapping minute amounts of metal ions present in the solution. The chelating agent may include, for example, citric acid or a salt thereof such as sodium citrate. The amount of the chelating agent may be in the range of from approximately 10% to 80%, preferably from approximately 20% to 50%, with respect to the amount of the water-soluble aluminum compound, although the amount of the chelating agent may be varied with the kind or the amount of the water-soluble aluminum compound, or the like. In a further embodiment the chelating agent is contained at a rate of 0.1% to 5%.

In addition, sodium hydrogen sulfite to be employed as the antioxidant for the curing injectable composition in the solution form according to the present invention may be contained at a rate ranging usually from 0.05% to 0.5%, preferably from 0.1% to 0.3%, with respect to the total weight of the ingredients of the injectable composition in the solution form, excluding distilled water. Particularly, if the sodium hydrogen sulfite would be contained in a lesser concentration with respect to the amount of the tannic acid, the resulting injectable composition in the solution form may cause precipitating and it cannot accomplish the desired effects sought to be achieved by the present invention.

In order to make the composition according to the present invention more stable, there may be added, as needed, the polyvalent alcohol and/or the saccharide, which are or is conventionally employed for curing injectable compositions. As the polyvalent alcohol and/or the saccharide to be used for the present invention, there may be mentioned glucose, glycerin, fructose, xylitol, mannose, mannitol, galactose, dextran and the like. Particularly, dextran has the action of raising the viscosity of the resulting compositions. The polyvalent alcohol and/or the saccharide may be employed singly or in combination of two or more. Further, the amount of the polyvalent alcohol and/or the saccharide is not limited to a particular one as long as the polyvalent alcohol and/or the saccharide may be contained at such a rate so as to raise the osmosis of the resulting injectable preparations by approximately three times to fifteen times, preferably from approximately four times to eight times, that of physiological saline. In addition, the polyvalent alcohol and/or the saccharide are or is preferably contained in the range of from approximately 3% to 20% preferably from approximately 5% to 15%, as the effective concentration in the injectable preparations.

Further, the injectable compositions in the solution form according to the present invention may contain another component which hitherto has been conventionally employed as an ingredient for compositions, such as an agent for increasing viscosity of a solution, e. g. dextran or the like, or an antiseptic agent, e. g. phenol, benzyl alcohol, benzalkonium chloride, p-aminobenzoic acid ester or the like. These components may optionally be employed within the range that does not substantially affect the effects of the compositions adversely.

In accordance with the present invention, it is of significance in terms of storage of the resulting preparations that the liquid property of the injectable preparations containing the composition is adjusted to be from pH 1.0 to pH 3.5, preferably from pH 2.0 to pH 3.0.

When the injectable compositions in the solution form according to the present invention can be prepared by means of the method according to the present invention, the liquid properties of the compositions may be usually set within the above-defined range without special adjustment and, in this case it is not particularly required to adjust the liquid properties of the resulting injectable preparations after or before the preparation of the compositions. It is also possible to adjust the liquid properties of the compositions, as needed, to the optimal level with a pharmacologically non-toxic acid or alkali, which are conventionally used for the formulation of the injectable preparations. Such agents may include, for example, a mineral acid such as hydrochloric acid or sulfuric acid, an organic acid such as citric acid, sodium hydrogen carbonate, sodium hydroxide or the like. The preparations having the liquid properties within the range as defined hereinabove can be stored in an extremely stable manner for a long period of time without causing any coloring or depositing or precipitating.

In order to prepare the stable injectable compositions in the solution form for treating the affected tissues according to the present invention from the components as described hereinabove, it is necessary to formulate each of the components in accordance with the order and conditions of formulation, as will be described hereinafter, with the properties of each component taken into consideration.

Specifically, the compositions according to the present invention can be prepared by formulating the sodium hydrogen sulfite, the water-soluble aluminum compound and the chelating agent in an optional order into a formulation and adding tannic acid to the resulting formulation.

In addition, the polyvalent alcohol and/or the saccharide may be added to the formulation or a mixture prepared by adding tannic acid to the formulation.

Alternatively, the compositions for treating the affected tissues according to the present invention may be prepared by separately forming a formulation by admixing the water-soluble aluminum compound with the chelating agent and a formulation by admixing tannic acid with the sodium hydrogen sulfite and then combining the two formulations together into the compositions.

In this case, too, the polyvalent alcohol and/or the saccharide may be added to either one or both of the formulations prepared in the alternative manner as have been described hereinabove or the mixture obtained by combining the two formulations.

In summary, the methods for the preparation of the compositions for treating the affected tissues in accordance with the present invention may comprise, in one aspect of the method, adding tannic acid to the formulation prepared by admixing sodium hydrogen sulfite with all the components other than tannic acid and sodium hydrogen sulfite in an optional way or, in an alternative aspect of the method, separately preparing the formulation by admixing the water-soluble aluminum compound with the chelating agent and the another formulation by admixing the tannic acid with the sodium hydrogen sulfite and then combining the formulation together with the another formulation into the mixture and, as needed, adding the polyvalent alcohol and/or the saccharide to the formulation or formulations or to the mixture at any stage of preparation. By formulating each of the components in the manner as described hereinabove, the oxidation of tannic acid can be prevented as well as the direct reaction of tannic acid with the metal ions such as the aluminum ions derived from the water-soluble aluminum compound can also be prevented, thereby enabling the formation of the stable compositions for treating the affected tissues according to the present invention in a constant manner.

In the method for the preparation of the compositions for treating the affected tissues according to the present invention, the pH range of the compositions can be adjusted, as needed, at any stage of formulation or admixture of the components so as for the resulting injectable preparations to demonstrate the liquid properties within the above-defined level, i. e. from pH 1.0 to pH 3.5. More specifically, when the compositions are prepared by adding tannic acid to the formulation prepared by admixing all the components other the tannic acid, the liquid properties of the injectable preparations can be adjusted at any or every stage of formulation or admixture by admixing the water-soluble aluminum compound and the chelating agent with sodium hydrogen sulfite and admixing tannic acid to the resulting formulation and adding the polyvalent alcohol and/or the saccharide to the resulting mixture as needed. Alternatively, when the compositions are prepared by admixing the formulation consisting of the water-soluble aluminum compound and the chelating agent with the formulation consisting of the tannic acid and the sodium hydrogen sulfite, the liquid properties of the injectable preparations can also be adjusted at any or every stage of formulation or admixture to the above-defined level by admixing the resulting formulations together with each other to yield the mixture and adding the polyvalent alcohol and/or the saccharide to the resulting mixture as needed.

In the methods for the preparation of the compositions for treating the affected tissues according to the present invention, it is preferred that any or every component of the composition is formulated with each other under atmosphere of an inert gas. As the inert gases to be used for this purpose, there may preferably be mentioned, for example, nitrogen gases.

Further, it is preferred that the compositions according to the present invention are prepared by formulating each of the components under conditions under which oxygen does not exist in an atmosphere or in water to be used in no substantial amount or in an amount restricted within the level that does not adversely affect the resulting compositions. Such level may be, for example, $1/1,000$ or less with respect to the level in a stationary state.

The compositions thus prepared in the manner as described hereinabove are then filtered and sterilized by means of conventional methods and filled in a container such as colorless hard glass ampoules or glass bottles. They are then sterilized by high-pressure steam, as needed, and stored in a cold place.

In accordance with the method for the preparation of the compositions for treating the affected tissues, it is preferred that each or every step of the method be carried out in the presence of inert gases such as nitrogen gases. The oxygen dissolved in the injectable preparations are usually removed by conventional methods and the air present in the injectable preparations is replenished with nitrogen gases.

The compositions according to the present invention can be lyophilized by conventional methods. They also can be applied by dissolving the components in distilled water in site. In this case, a solution prepared by dissolving the polyvalent alcohol and/or the saccharide may also be used as a solution for use in dissolving the compositions in site.

The compositions for treating the affected tissues according to the present invention have the peculiar properties of killing the affected tissues of the digestive organs, particularly the large intestine and rectum, upon contact with the locations of the tissues affected with the piles or hemorrhoids, such as internal piles or hemorrhoids, archoptoma or the like, the uplift affected tissues, the tissues affected with hepatic tumor and the like.

The compositions according to the present invention can demonstrate the strong action of killing the cells of the affected tissues while holding the states or shapes of the cells. In other words, it is anticipated that the compositions can kill the cells of the affected tissues upon contact by application and then cause the killed cells to fall off from the normal tissues. By allowing the killed cells to fall off from the normal tissues, the compositions according to the present invention can sclerose the affected tissues and treat them in mild conditions.

The compositions for treating the affected tissues of the digestive organ according to the present invention will be described in more detail by way of examples.

EXAMPLE NO. 1

The composition for treating the affected tissues according to this example contains the following components:

| | |
|---|---|
| Aluminum potassium sulfate | 400 mg |
| Sodium citrate | 150 mg |
| Sodium hydrogen sulfite | 15 mg |
| Tannic acid | 15 mg |
| Dextran 40 | 70 mg |
| Glycerin | 1,000 mg |
| Injectable distilled water | To make 10 ml |

The injectable distilled water prepared so as to comply with *Pharmacopedia Japonica* was treated to remove dissolved oxygen by heating it at 100° C. for five minutes. After the completion of heating, nitrogen gases were introduced into the treated water and allowed to cool to room temperature.

Separately, the total amount of dextran 40 was fully dissolved in an appropriate solvent in advance because it is less soluble to the solution for use.

The total amount of sodium hydrogen sulfite was dissolved into an appropriate amount of the injectable distilled water, and the resulting solution was added with the dextran solution and then with sodium citrate, followed by the addition thereto of the total amounts of aluminum potassium sulfate and glycerin. To the resulting solution was added the total amount of tannic acid. The formulation of each of the components was carried out while nitrogen gases had been kept introduced thereinto. The resulting solution was stirred for about 30 minutes and filtered through a filter. Into the filtrate were introduced nitrogen gases to yield the objective composition. The composition had a pH of 2.7.

The resulting solution was then filled in glass vials or ampoules. Before and after filling, the air in the solution was replenished with nitrogen gases and the vials or ampoules were sealed, followed by storage in a cold dark place.

EXAMPLE NO. 2

The composition having the same components as the one prepared in Example No. 1 was prepared in substantially the same manner as in Example No. 1 with the exception that the dextran solution, sodium citrate, aluminum potassium sulfate and glycerin were added in the order of sodium citrate, aluminum potassium sulfate, glycerin and the dextran solution. The resulting composition had a pH of 2.6.

EXAMPLE NO. 3

The composition having the same components as the one prepared in Example No. 1 was prepared in substantially the same manner as in Example No. 1 with the exception that the dextran solution, sodium citrate, aluminum potassium sulfate and glycerin were added in the order of aluminum potassium sulfate, glycerin, the dextran solution and sodium citrate. The resulting composition had a pH of 2.7.

EXAMPLE NO. 4

The composition having the same components as the one prepared in Example No. 1 was prepared in substantially the same manner as in Example No. 1 with the exception that the dextran solution, sodium citrate, aluminum potassium sulfate and glycerin were added in the order of glycerin, the dextran solution, sodium citrate and aluminum potassium sulfate. The resulting composition had a pH of 2.7.

EXAMPLE NO. 5

The composition for treating the affected tissues according to this example contained the following components:

| | |
|---|---|
| Aluminum chloride | 400 mg |
| Tannic acid | 15 mg |
| Sodium citrate | 150 mg |
| Dextran 40 | 70 mg |
| Sodium hydrogen sulfite | 15 mg |
| Mannitol | 1,500 mg |
| Injectable distilled water | To make 10 ml |

The injectable distilled water was treated to remove dissolved oxygen by heating at 100° C. for five minutes. After the completion of heating, nitrogen gases were introduced into the treated water and allowed to cool to room temperature.

The total amount of sodium hydrogen sulfite was dissolved into an appropriate amount of the injectable distilled water thermally treated, and the resulting solution was added with the dextran solution prepared separately and then with sodium citrate, followed by the addition thereto of the total amounts of aluminum chloride and mannitol. To the resulting solution was then added the total amount of tannic acid yielding a solution. The formulation of each of the components was carried out while nitrogen gases had been kept introduced thereinto. The resulting solution was stirred for about 30 minutes, added with hydrochloric acid to adjust its pH to pH 3.0 and filtered through a filter. Into the filtrate were introduced nitrogen gases to yield the objective composition.

The resulting solution was then filled in glass vials or ampoules. Before and after filling, the air in the solution was replenished with nitrogen gases and the vials or ampoules. Before and after filling, the air in the solution was replenished with nitrogen gases and the vials or ampoules were sealed, followed by storage in a cold dark place.

EXAMPLE NO. 6-1

The composition of this example contained the components as follows:

| | |
|---|---|
| Aluminum sulfate | 400 mg |
| Tannic acid | 15 mg |
| Sodium citrate | 150 mg |
| Dextran 40 | 70 mg |
| Sodium hydrogen sulfite | 15 mg |
| Fructose | 2,000 mg |
| Injectable distilled water | To make 10 ml |

The injectable preparations were prepared by formulating each of the components in substantially the manner as in Example No. 5 with the exception that aluminum chloride was replaced with aluminum sulfate and mannitol was replaced with fructose. The resulting composition had a pH of 2.7.

EXAMPLE NO. 6-2

The composition of this example contained the components as follows:

| | |
|---|---|
| Aluminum sulfate | 400 mg |
| Tannic acid | 75 mg |
| Sodium citrate | 150 mg |
| Dextran 40 | 70 mg |
| Sodium hydrogen sulfite | 15 mg |
| Glycerin | 1,000 mg |
| Injectable distilled water | To make 10 ml |

The injectable preparations were prepared by dissolving each of the above ingredients in a small amount of injectable distilled water and the resulting solutions were mixed with each other to make the total volume of the mixture 10 ml. The resulting mixture was then adjusted with sulfuric acid to pH 2.7 and poured into a glass bottle, followed by the deaeration of dissolved oxygen in the solution, the replenishment of the air therein with nitrogen gases, and sterilization with high-pressure steam. The glass bottle was stored in cold dark place.

EXAMPLE NO. 7

The composition of this example contained the components as follows:

| | |
|---|---|
| Aluminum carbonate | 200 mg |
| Tannic acid | 15 mg |
| Sodium citrate | 150 mg |
| Dextran 40 | 70 mg |
| Sodium hydrogen sulfite | 15 mg |
| Xylitol | 2,000 mg |
| Injectable distilled water | To make 10 ml |

The injectable preparations were prepared in substantially the same manner as in Example No. 5 with the exception that aluminum chloride was replaced with aluminum carbonate and mannitol was replaced with xylitol. The resulting composition was treated with sulfuric acid to give a pH of 2.7.

EXAMPLE NO. 8

The composition of this example contained the components as follows:

| | |
|---|---|
| Aluminum acetate | 200 mg |
| Tannic acid | 15 mg |
| Sodium citrate | 150 mg |
| Dextran 40 | 70 mg |
| Sodium hydrogen sulfite | 15 mg |
| Glucose | 3,000 mg |
| Injectable distilled water | To make 10 ml |

The injectable preparations were prepared in substantially the same manner as in Example No. 5 with the exception that aluminum chloride was replaced with aluminum acetate and mannitol was replaced with glucose. The resulting composition was treated with sulfuric acid to give a pH of 2.7.

EXAMPLE NO. 9

The composition for treating the affected tissues according to this example contained the components as follows:

| | |
|---|---|
| Aluminum potassium sulfate | 400 mg |
| Tannic aaid | 15 mg |
| Sodium citrate | 150 mg |
| Dextran 40 | 70 mg |
| Sodium hydrogen sulfite | 10 mg |
| Glycerin | 1,000 mg |
| Injectable distilled water | To make 10 ml |

The injectable preparations were prepared by formulating the above components in substantially the same manner as in Example No. 1. The resulting composition was adjusted with sulfuric acid to a pH of 2.7.

EXAMPLE NO. 10

The composition for treating the affected tissues according to this example contained the components as follows:

| | |
|---|---|
| Aluminum potassium sulfate | 400 mg |
| Tannic acid | 30 mg |
| Sodium citrate | 150 mg |
| Dextran 40 | 70 mg |
| Sodium hydrogen sulfite | 30 mg |
| Glycerin | 1,000 mg |
| Injectable distilled water | To make 10 ml |

The injectable preparations were prepared by formulating the above components in substantially the same manner as in Example No. 1. The resulting composition was adjusted with sulfuric acid to pH 2.8.

EXAMPLE NO. 11

The composition for treating the affected tissues according to this example contained the components as follows:

| | |
|---|---|
| Aluminum potassium sulfate | 400 mg |
| Tannic acid | 50 mg |
| Sodium citrate | 150 mg |
| Dextran 40 | 70 mg |
| Sodium hydrogen sulfite | 70 mg |
| Glycerin | 1,000 mg |
| Injectable distilled water | To make 10 ml |

The injectable preparations were prepared by formulating the above components in substantially the same manner as in Example No. 1. The resulting composition was adjusted with sulfuric acid to pH 2.7.

EXAMPLE NO. 12

The composition for treating the affected tissues according to this example contained the components as follows:

| | |
|---|---|
| Aluminum potassium sulfate | 400 mg |
| Tannic acid | 70 mg |
| Sodium citrate | 150 mg |
| Dextran 40 | 70 mg |
| Sodium hydrogen sulfite | 70 mg |
| Glycerin | 1,000 mg |
| Injectable distilled water | To make 10 ml |

The injectable preparations were prepared by formulating the above components in substantially the same manner as in Example No. 1. The resulting composition had a pH of 3.2.

EXAMPLE NO. 13

The composition for treating the affected tissues according to this example contained the components as follows:

| | |
|---|---|
| Aluminum potassium sulfate | 400 mg |
| Tannic acid | 90 mg |
| Sodium citrate | 150 mg |
| Dextran 40 | 70 mg |
| Sodium hydrogen sulfite | 100 mg |
| Glycerin | 1,000 mg |
| Injectable distilled water | To make 10 ml |

The injectable preparations were prepared by formulating the above components in substantially the same manner as in Example No. 1. The resulting composition was adjusted with sulfuric acid to a pH of 2.7.

EXAMPLE NO. 14

The composition for treating the affected tissues according to this example contained the components as follows:

| | |
|---|---|
| Aluminum potassium sulfate | 400 mg |
| Tannic acid | 100 mg |
| Sodium citrate | 150 mg |
| Dextran 40 | 70 mg |
| Sodium hydrogen sulfite | 100 mg |
| Glycerin | 1,000 mg |
| Injectable distilled water | To make 10 ml |

The injectable preparations were prepared by formulating the above components in substantially the same manner as in Example No. 1. The resulting composition was adjusted with sulfuric acid to pH 2.7.

EXAMPLE NO. 15

The composition for treating the affected tissues according to this example contained the components as follows:

| | |
|---|---|
| Aluminum potassium sulfate | 400 mg |
| Tannic acid | 120 mg |
| Sodium citrate | 150 mg |
| Sodium hydrogen sulfite | 140 mg |
| Glycerin | 1,200 mg |
| Injectable distilled water | To make 10 ml |

The injectable preparations were prepared by formulating the above components in substantially the same manner as in Example No. 1. The resulting composition was adjusted with sulfuric acid to pH 2.7.

EXAMPLE NO. 16

The composition for treating the affected tissues according to this example contained the components as follows:

| | |
|---|---|
| Aluminum potassium sulfate | 400 mg |
| Tannic acid | 15 mg |
| Sodium citrate | 300 mg |
| Sodium hydrogen sulfite | 20 mg |
| Mannitol | 3,000 mg |
| Injectable distilled water | To make 10 ml |

The injectable preparations were prepared in substantially the same manner as in Example No. 1 with the exception that dextran was not used and glycerin was replaced with mannitol. The resulting composition was adjusted with sulfuric acid to a pH of 2.7.

EXAMPLE NO. 17

The composition for treating the affected tissues according to this example contained the components as follows:

| | |
|---|---|
| Aluminum potassium sulfate | 400 mg |
| Sodium citrate | 50 mg |
| Sodium hydrogen sulfite | 15 mg |
| Tannic acid | 15 mg |
| Glycerin | 1,100 mg |
| Injectable distilled water | To make 10 ml |

The injectable distilled water prepared so as to comply with *Pharmacopedia Japonica* was treated to remove dissolved oxygen by heating at 100° C. for five minutes. After the completion of heating, nitrogen gases were introduced into the treated water and allowed to cool to room temperature.

The total amount of sodium hydrogen sulfite was dissolved into an appropriate amount of the injectable distilled water, and the resulting solution was added with sodium citrate, followed by the addition thereto of the total amounts of aluminum potassium sulfate and glycerin. To the resulting solution was added the total amount of tannic acid. The formulation of each of the components was carried out while nitrogen gases had been kept introduced thereinto. The resulting solution was stirred for about 30 minutes, adjusted with sulfuric acid to demonstrate a pH of 3.1, and filtered through a filter. Into the filtrate were introduced nitrogen gases to yield the objective composition.

The resulting solution was then filled in glass vials or ampoules. Before and after filling, the air in the solution was replenished with nitrogen gases and the vials or ampoules were sealed, followed by storage in a cold dark place.

EXAMPLE NO. 18

The composition for treating the affected tissues according to this example contained the components as follows:

| | |
|---|---|
| Aluminum potassium sulfate | 400 mg |
| Sodium citrate | 100 mg |
| Sodium hydrogen sulfite | 15 mg |
| Tannic acid | 15 mg |
| Dextran 40 | 100 mg |
| Injectable distilled water | To make 10 ml |

The injectable distilled water prepared so as to comply with *Pharmacopedia Japonica* was treated to remove dissolved Oxygen by heating at 100° C. for five minutes. After the completion of heating, nitrogen gases were introduced into the treated water and allowed to cool to room temperature.

The total amount of sodium hydrogen sulfite was dissolved into an appropriate amount of the injectable distilled water, and the resulting solution was added with the total amounts of the dextran solution separately prepared and sodium citrate, followed by the addition thereto of the total amount of aluminum potassium sulfate. To the resulting solution was added the total amount of tannic acid. The formulation of each of the components was carried out while nitrogen gases had been kept introduced thereinto. The resulting solution was stirred for about 30 minutes, adjusted with sulfuric acid to give a pH of 2.8, and filtered through a filter. Into the filtrate were introduced nitrogen gases to yield the objective composition.

The resulting solution was then filled in glass vials or ampoules. Before and after filling, the air in the solution was replenished with nitrogen gases and the vials or ampoules were sealed, followed by storage in a cold dark place.

EXAMPLE NO. 19

This example provided the injectable preparations for treating the affected tissues for use in site, which contained the components as follows:

| | |
|---|---|
| Agent I: | |
| Tannic acid | 15 ml |
| Sodium hydrogen sulfite | 15 ml |
| Injectable distilled water | To make 10 ml |
| Agent II: | |
| Aluminum potassium sulfate | 400 mg |
| Sodium citrate | 150 mg |
| Dextran 40 | 70 mg |

| | |
|---|---|
| Glycerin | 1,000 mg |
| Injectable distilled water | To make 10 ml |

The above Agent I was prepared by adding the total amount of tannic acid in the presence of nitrogen gases to a solution prepared by dissolving sodium hydrogen sulfite in the injectable distilled water. On the other hand, the above agent II was prepared by dissolving sodium citrate in the injectable distilled water in the presence of nitrogen gases and adding thereto aluminum potassium sulfate in the presence of nitrogen gases, followed by addition thereto of dextran and glycerin. The Agents I and II prepared in the above manner were combined into injectable preparations for use in site by adding the Agent II to the Agent I. The injectable preparations were adjusted with sulfuric acid to a pH of 2.7.

EXAMPLE NO. 20

This example provided the injectable preparations for treating the affected tissues for use in site which contained the components as follows:

| Agent I: | |
|---|---|
| Aluminum potassium sulfate | 400 mg |
| Sodium citrate | 150 mg |
| Sodium hydrogen sulfite | 20 mg |
| Injectable distilled water | To make 10 ml |
| Agent II: | |
| Tannic acid | 20 mg |
| Glycerin | 1,200 mg |
| Injectable distilled water | To make 10 ml |

The above Agent I was prepared by adding the total amounts of sodium hydrogen sulfite and sodium citrate in the presence of nitrogen gases to the injectable distilled water and then aluminum potassium sulfate to the resulting solution in the presence of nitrogen gases. Separately, the above agent II was prepared by dissolving glycerin and tannic acid in this order in the injectable distilled water in the presence of nitrogen gases. The Agents I and II prepared in the manner as described hereinabove were combined in site for use as injectable preparations by adding the Agent II to the Agent I. The injectable preparations were adjusted with sulfuric acid, as needed, to a pH of 2.7.

EXAMPLE NO. 21

This example provided the injectable preparations for treating the affected tissues for use in site which contained the components as follows:

| Agent I: | |
|---|---|
| Aluminum potassium sulfate | 400 mg |
| Sodium citrate | 150 mg |
| Injectable distilled water | To make 10 ml |
| Agent II: | |
| Tannic acid | 50 mg |
| Sodium hydrogen sulfite | 100 mg |
| Injectable distilled water | To make 10 ml |

The above Agent I was prepared by adding the total amount of sodium citrate to the injectable distilled water and then aluminum potassium sulfate to the resulting solution in the presence of nitrogen gases. On the other hand, the above agent II was prepared by dissolving sodium hydrogen sulfite and tannic acid in the injectable distilled water in the presence of nitrogen gases. The above Agent III was prepared in substantially the same manner as above by dissolving sodium hydrogen sulfite in the injectable distilled water in the presence of nitrogen gases. The Agents I and II prepared in the above manner were used as injectable preparations by adding the Agent II to the Agent I. The injectable preparations were adjusted to a pH of 2.7.

EXAMPLE NO. 22

This example provided the injectable preparations for treating the affected tissues for use in site which contained the components as follows:

| Agent I: | |
|---|---|
| Aluminum potassium sulfate | 400 mg |
| Sodium citrate | 150 mg |
| Tannic acid | 15 mg |
| Sodium hydrogen sulfite | 15 mg |
| Injectable distilled water | To make 10 ml |
| Agent II: | |
| Glycerin | 1,000 mg |
| Dextran | 70 mg |
| Injectable distilled water | To make 10 ml |

The above Agent I was prepared by adding the total amount of sodium citrate to the injectable distilled water and then aluminum potassium sulfate to the resulting solution in the presence of nitrogen gases. To the resulting solution was added a solution prepared by dissolving the total amounts of sodium hydrogen sulfite and tannic acid in the injectable distilled water in the presence of nitrogen gases. The resulting Agent I had a pH of 2.7 and was lyophilized in conventional manner, followed by storage for one month in a cold dark place.

The injectable preparations were prepared for use in site by adding the Agent II to the Agent I and used for tests for stability of the preparations in a way as will be described hereinafter.

COMPARATIVE EXAMPLE NO. 1

The composition prepared in Example No. 1 was adjusted with sodium hydroxide to pH 4.7 for comparative purposes.

COMPARATIVE EXAMPLE NO. 2

The composition was prepared by adding dextran, aluminum potassium sulfate, glycerin and tannic acid in this consecutive order in the injectable distilled water in the presence of nitrogen gases. The resulting injectable preparations in the solution form were adjusted with sulfuric acid to pH 2.7.

COMPARATIVE EXAMPLE NO. 3

The injectable preparations of this comparative example was prepared which contained the following components:

| | |
|---|---|
| Aluminum potassium sulfate | 4.0 g |
| Tannic acid | 0.15 g |
| Sodium citrate | 1.5 g |
| Dextran | 10 ml |

| | |
|---|---|
| Trichlorobutanol | 0.5 g |
| Glycerin | 10 ml |
| Injectable distilled water | To make 100 ml |

The injectable preparations in the solution form were prepared by adding each of the above components to the injectable distilled water in the manner as enumerated hereinabove and the resulting preparations were adjusted with sodium hydroxide to pH 4.7.

COMPARATIVE EXAMPLE NO. 4-1

The sclerosing agent having the same composition as disclosed in Japanese Patent Unexamined Publication (Kokai) No. 4-225.920 as the Comparative Preparation Formulation Example No. 1 was prepared in substantially the same manner as disclosed in this publication. More specifically, the composition having the same components was formulated in the same order and in substantially the same manner as disclosed in this publication to give injectable preparations which were then adjusted with sodium hydroxide to pH 4–5. The resulting injectable preparations in the solution form were filled by a 10 ml portion in each of colorless hard glass ampoules which in turn were treated in order to replenish the air in the ampoules with nitrogen gases and then sterilized with high pressure steam in conventional manner.

COMPARATIVE EXAMPLE NO. 4-2

An injectable preparation was prepared in substantially the same manner as Comparative Example No. 3 above, which had the same components as Comparative Example No. 3 excluding sodium citrate and sodium hydrogen sulfite therefrom. The resulting preparation was adjusted with sulfuric acid to pH 2.7.

COMPARATIVE EXAMPLE NO. 5

The sclerosing agent having the same composition as disclosed in Japanese Patent Unexamined Publication (Kokai) No. 4-225.920 as the Comparative Preparation Formulation Example No. 3 was prepared in substantially the same manner as disclosed in this publication. More specifically the composition having the same components was formulated in substantially the same manner as disclosed in this publication to yield injectable preparations which were then adjusted with sodium hydroxide to pH 4–5. The resulting injectable preparations in the solution form were filled by a 10 ml portion in each of colorless hard glass ampoules which in turn were treated in order to replenish the air in the ampoules with nitrogen gases and then sterilized with high pressure steam in conventional manner.

COMPARATIVE EXAMPLE NO. 6

The sclerosing agent having the same composition as disclosed in Japanese Patent Unexamined Publication (Kokai) No. 4-225.920 as the Comparative Preparation Formulation Example No. 5 was prepared in substantially the same manner as disclosed in the publication. More specifically, the composition having the same components was formulated in the same order and in substantially the same manner as disclosed in the publication to give the composition which was then adjusted with sulfuric acid to pH 2.7. The resulting aqueous solution was filled by a 50 ml portion in each of colorless hard glass vials which in turn were treated in order to replenish the gases in the vials with nitrogen gases and then sterilized with high pressure steam in conventional manner.

COMPARATIVE EXAMPLE NO. 7

Into a test tube were poured simultaneously the same components in the same amounts as Example No. 1, and injectable distilled water was added with stirring to the mixture to make the total amount 10 ml. The resulting composition in the solution form became turbid in white color and caused precipitating as the time passed by.

COMPARATIVE EXAMPLE NO. 8

The same amounts of the same components as indicated in Example No. 1 above were dissolved with stirring in the same order in injectable distilled water. The resulting composition in the solution form became turbid in white color and caused precipitating as the time has elapsed.

COMPARATIVE EXAMPLE NO. 9

The same amounts of the same components as indicated in Example No. 1 above were dissolved with stirring in the same order in injectable distilled water. The resulting solution became turbid in white color and caused precipitating as the time has passed by.

COMPARATIVE EXAMPLE NO. 10

For the preparation of the composition having the same components and containing the same amounts, respectively, as Example No. 1 above, dextran and glycerin were admixed with injectable distilled water, followed by the addition of aluminum potassium sulfate and tannic acid to the resulting mixture. To the resulting solution were added sodium citrate and sodium hydrogen sulfite to give injectable preparations. It was found that this solution turned turbid in white color at the time when tannic acid was added and it soon caused precipitates in a dark brown color.

COMPARATIVE EXAMPLE NO. 11

A solution (Agent I) was prepared by dissolving 400 mg of aluminum potassium sulfate and 400 mg of tannic acid in 10 ml of injectable distilled water in the presence of nitrogen gases. Separately, a solution (Agent II) was prepared by dissolving 70 mg of dextran, 1,000 mg of glycerin, 15 mg of sodium citrate and 15 mg of sodium hydrogen sulfite in this order in 10 ml of injectable distilled water in the presence of nitrogen gases. The injectable preparations were prepared by admixing Agent I with Agent II. The resulting injectable preparations were found to turn turbid in pale brown color at the time when tannic acid was added to aluminum potassium sulfate in the Agent I and the resulting injectable composition in the solution form caused precipitates in dark brown color within short.

The injectable preparations in the solution form according to the present invention prepared in the manner as described hereinabove were subjected to tests for stability of preparations.

TESTS FOR STABILITY OF PREPARATIONS

After the injectable preparations in the solution form prepared in the above-mentioned Examples were adjusted to give the pH ranges as defined hereinabove, five colorless hard glass vials were aseptically filled with 10 ml of each of the injectable compositions in the solution form and the air in the vials was replenished with nitrogen gas under vacuum conditions. The vials were then exposed to white light with 1,000 lux at 400° C. and visual observations were made as to coloring and the extent of depositing. Before carrying out the tests for stability of injectable preparations, each of the injectable compositions in the solution form were found colorless or transparent, yellowish and slightly viscous. The test results are shown in Table 1 below.

TABLE 1

Results of Tests for Stability of Preparations

| Example Nos. | Storage Period of Time (Months) | | | | | |
|---|---|---|---|---|---|---|
| | 0 | 1 | 2 | 3 | 6 | 12 |
| No. 1 | Colorless or faintly yellowish | Colorless or faintly yellowish | Colorless or faintly yellowish | Colorless or faintly yellowish | Colorless or faintly yellowish | Colorless or faintly yellowish |
| No. 2 | Colorless or faintly yellowish | Colorless or faintly yellowish | Colorless or faintly yellowish | Colorless or faintly yellowish | Colorless or faintly yellowish | Colorless or faintly yellowish |
| No. 3 | Colorless or faintly yellowish | Colorless or faintly yellowish | Colorless or faintly yellowish | Colorless or faintly yellowish | Colorless or faintly yellowish | Colorless or faintly yellowish |
| No. 4-1 | Colorless or faintly yellowish | Colorless or faintly yellowish | Colorless or faintly yellowish | Colorless or faintly yellowish | Colorless or faintly yellowish | Colorless or faintly yellowish |
| No. 4-2 | Colorless or faintly yellowish | Colorless or faintly yellowish | Colorless or faintly yellowish | Colorless or faintly yellowish | Colorless or faintly yellowish | Colorless or faintly yellowish |
| No. 5 | Colorless or faintly yellowish | Colorless or faintly yellowish | Colorless or faintly yellowish | Colorless or faintly yellowish | Colorless or faintly yellowish | Colorless or faintly yellowish |
| No. 6 | Colorless or faintly yellowish | Colorless or faintly yellowish | Colorless or faintly yellowish | Colorless or faintly yellowish | Colorless or faintly yellowish | Colorless or faintly yellowish |
| No. 7 | Colorless or faintly yellowish | Colorless or faintly yellowish | Colorless or faintly yellowish | Colorless or faintly yellowish | Colorless or faintly yellowish | Colorless or faintly yellowish |
| No. 8 | Colorless or faintly yellowish | Colorless or faintly yellowish | Colorless or faintly yellowish | Colorless or faintly yellowish | Colorless or faintly yellowish | Colorless or faintly yellowish |
| No. 9 | Pale yellow | Pale yellow | Pale yellow | Pale yellow | Pale yellow | Pale yellow |
| No. 10 | " | " | " | " | " | " |
| No. 11 | " | " | " | " | " | " |
| No. 12 | " | " | " | " | " | " |
| No. 13 | " | " | " | " | " | " |
| No. 14 | " | " | " | " | " | " |
| No. 15 | " | " | " | " | " | " |
| No. 16 | Pale yellow | Pale yellow | Pale yellow | Pale yellow | Pale yellow | Pale yellow |
| No. 17 | " | " | " | " | " | " |
| No. 18 | " | " | " | " | " | " |
| No. 19 | " | " | " | " | " | " |
| No. 20 | " | " | " | " | " | " |
| No. 21 | " | " | " | " | " | " |
| No. 22 | " | " | " | " | " | " |
| Comparative Example 1 | Colorless or faintly yellowish | White deposit | White deposit | White deposit | White deposit | White deposit |
| Comparative Example 2 | Colorless or faintly yellowish | Colored deposit | Colored deposit | Colored deposit | Colored deposit | Colored deposit |
| Comparative Example 3 | Colorless or faintly yellowish | White deposit | White deposit | Colored deposit | Colored deposit | Colored deposit |
| Comparative Example 4-1 | Colorless or faintly yellowish | Colored deposit | Colored deposit | Colored deposit | Colored deposit | Colored deposit |
| Comparative Example 4-2 | Colorless or faintly yellowish | Colored deposit | Colored deposit | Colored deposit | Colored deposit | Colored deposit |
| Comparative Example 5 | Colorless or faintly yellowish | Colored deposit | Colored deposit | Colored deposit | Colored deposit | Colored deposit |
| Comparative Example 6 | Colorless or faintly yellowish | Colored deposit | Colored deposit | Colored deposit | Colored deposit | Colored deposit |
| Comparative Example 7 | Colorless or faintly yellowish | Colored deposit | Colored deposit | Colored deposit | Colored deposit | Colored deposit |
| Comparative Example 6 | Colorless or faintly | Colored deposit | Colored deposit | Colored deposit | Colored deposit | Colored deposit |

TABLE 1-continued

Results of Tests for Stability of Preparations

| Example Nos. | Storage Period of Time (Months) | | | | | |
|---|---|---|---|---|---|---|
| | 0 | 1 | 2 | 3 | 6 | 12 |
| Comparative Example 9 | Colorless or faintly yellowish | Colored deposit | Colored deposit | Colored deposit | Colored deposit | Colored deposit |
| Comparative Example 10 | Colorless or faintly yellowish | Colored deposit | Colored deposit | Colored deposit | Colored deposit | Colored deposit |
| Comparative Example 11 | Pale brown | Colored deposit | Colored deposit | Colored deposit | Colored deposit | Colored deposit |

Table 2 below shows the results of the tests for stability of the injectable preparations in substantially the same manner as with the injectable preparations tested above as shown in Table 1 above, with the exception that the temperature for storage was set at 60° C.

TABLE 2

Results of Tests for Stability of Preparations

| Example Nos. | Storage Period of Time (Months) | | | | | |
|---|---|---|---|---|---|---|
| | 0 | 1 | 2 | 3 | 6 | 12 |
| No. 1 | Colorless or faintly yellowish | Colorless or faintly yellowish | Colorless or faintly yellowish | Colorless or faintly yellowish | Colorless or faintly yellowish | Colorless or faintly yellowish |
| No. 2 | Colorless or faintly yellowish | Colorless or faintly yellowish | Colorless or faintly yellowish | Colorless or faintly yellowish | Colorless or faintly yellowish | Colorless or faintly yellowish |
| No. 3 | Colorless or faintly yellowish | Colorless or faintly yellowish | Colorless or faintly yellowish | Colorless or faintly yellowish | Colorless or faintly yellowish | Colorless or faintly yellowish |
| No. 4-1 | Colorless or faintly yellowish | Colorless or faintly yellowish | Colorless or faintly yellowish | Colorless or faintly yellowish | Colorless or faintly yellowish | Colorless or faintly yellowish |
| No. 8 | Colorless or faintly yellowish | Colorless or faintly yellowish | Colorless or faintly yellowish | Colorless or faintly yellowish | Colorless or faintly yellowish | Colorless or faintly yellowish |
| No. 9 | Pale yellow | Pale yellow | Pale yellow | Pale yellow | Pale yellow | Pale yellow |
| No. 10 | " | " | " | " | " | " |
| No. 11 | " | " | " | " | " | " |
| No. 12 | " | " | " | " | " | " |

Further, the compositions prepared in Comparative Example Nos. 5 and 7 by the procedures as described in Japanese Patent Unexamined Publication Kokai No. 4-225, 920 were found instable due to the presence of the extract from the medicinal plants used therefor so that they are decided as inappropriate for clinical administration. Hence, they were excluded from the tests for stability of the preparations.

In addition, they were decided as inappropriate as injectable preparations because they contain an edetoate.

ACUTE TOXICITY TESTS

The injectable preparation as prepared in Example No. 1 was administered intravenously (iv) or intraperitoneally (ip) to four groups of rats, each group consisting of ten male Wister-type rats weighing 200±20 grams. The results of death were observed in fourteen days after administration and the lethal dose ($LD_{50}$), i.e. the rate of a half of experimental animals died, was computed in accordance with the Richfield-Wilcockson method. It was found that the lethal dose ($LD_{50}$) was 8.3±0.5 ml/kg of the body weight of the tested rat, when it was administered intravenously (iv) and that the lethal dose ($LD_{50}$) was 30 ml/kg or more when it was administered intraperitoneally (ip).

Tests for Repair of Brain Aneurysm by Monkeys:

The injectable preparations in the solution form according to the present invention were tested in order to confirm whether they are effective for the repair of the brain aneurysm in monkeys.

The tests for repairing the brain aneurysm were carried out by using healthy nine monkeys with 10 years or more of age and divided into three groups of each three monkeys. Before the tests, each monkey was subjected to encephaloarteriography and it was confirmed that each had aneurysm having a size as large as its fifth finger in section.

For control, a solution containing equivalent amounts of physiological saline and an iodo contrast medium was slowly and gradually injected into the first group of monkeys as a control, at the rate of 0.1 ml/kg of the body weight of the testing monkey over the period of 10 minutes through a catheter introduced into the affected part through its arteriae carotis interna.

A solution containing equivalent amounts of the Example No. 1 and the iodine contrast medium was slowly and gradually injected into the second group of the testing monkeys at the rate of 0.1 ml/kg of the body weight of the testing monkey through a catheter in the same manner as above.

Further, a solution containing the Example No. 1 and the two-fold amount of the iodine contrast medium was injected slowly and gradually into the third group of monkeys at the rate of 0.1 ml/kg of the body weight of the testing monkey through a catheter in the same manner as above.

As a result of these tests, it was found that the ability of contrasting was slightly reduced when the contrast medium was diluted. No clinical problems, however, could be seen when the encephalo-arteriography was carried out using a digital substraction angiography device (DSA). Although it is of importance that no symptom of the defluxion of the nerves is caused to occur for the repair of the brain aneurysm, in addition to the normalization of the blood vessels at their swollen parts, it was found that the concentration of the injectable composition in the solution form served as a particularly significant factor in order to achieve the effects of causing no such symptom to occur. The test results are shown in Table 3 below.

TABLE 3

Test for Repairing Brain Aneurysm in Monkeys

| Group | No. | Abnormal Angiograph | Curing Effect | Symptom of Defluxion of Nerves | Comprehensive Effects |
|---|---|---|---|---|---|
| 1 | 1 | No change | None | None | Not effective |
|   | 2 | " | " | " | " |
|   | 3 | " | " | " | " |
| 2 | 1 | Remarkably improved | Remarkably improved | Recognized | " |
|   | 2 | Remarkably improved | Remarkably improved | " | " |
|   | 3 | Remarkably improved | Remarkably improved | " | " |
| 3 | 1 | Remarkably improved | Remarkably improved | None | Remarkable |
|   | 2 | Remarkably improved | Remarkably improved | " | " |
|   | 3 | Remarkably improved | Remarkably improved | " | " |

In order to confirm the effectiveness of the curing injectable preparations in the solution form according to the present invention for treating and curing the piles or hemorrhoids, the tests for treating and curing the hemorrhoids have been carried out in a manner as will be described hereinbelow.

Tests for Curing Hemorrhoids in Monkeys:

A hemorrhoid model in monkeys was formed in a manner as will be described below. In 10 ml of an injectable water was dissolved 0.1 mg of commercially available dry snake toxin, and a histolysis agent was prepared by adding 10 mg of hyaluronidase, 100 mg of chondroitin sulfate and a very small amount of epinephrine to the solution. Six monkeys with one year of age were divided into three groups of each two monkeys, and 3 ml of the histolysis agent was administered once per week to each monkey in the submucosa and the mucoderm of its rectum and the anal tract. The monkeys were fed with high protein feed with less fibrous materials, thereby reducing the intestinal vermiculation. Each of the monkeys was raised in a cage with a ring put on around its neck and their legs standing straight. As they grew in this state, they become always in a state of constipation and become accustomed to defecation with anger and the stool became small in amount and hard. The anal portion of each monkey was turned into a congestive state upon repetition of the defecation with anger, and the proctoptosis was caused upon defecation. This completed the hemorrhoid model in monkey.

Each monkey in the first group as a control was injected in the blood vessel knobs of its hemorrhoids with 10 ml of physiological saline. In the second group, each monkey was injected in the blood vessel knobs of its hemorrhoids with 10 ml of an injectable preparation in the solution form prepared by diluting the preparation formulation example No. 1 with an equivalent amount of physiological saline. In the third group, each monkey was injected in the blood vessel knobs of its hemorrhoids with 10 ml of an injectable preparation in the solution form prepared by diluting the preparation formulation example No. 6 with an equivalent amount of physiological saline. The test results are shown in Table 4 below.

TABLE 4

Tests for Curing Hemorrhoids in Monkeys

| Group | No. | Blood vessel knobs of hemorrhoids | Curing Effects |
|---|---|---|---|
| 1 | 1 | Not changed | Not effective |
|   | 2 | " | " |
| 2 | 1 | Disappeared | Remarkable effective |
|   | 2 | " | " |
| 3 | 1 | " | " |
|   | 2 | " | " |

In order to confirm the effectiveness of the curing injectable preparation in the solution form according to the present invention for curing the hepatic tumor, the tests for treating and curing the hepatic tumor in dogs have been carried out in a manner as will be described hereinbelow.

Tests for Curing Hepatic Tumor in Dogs:

Twelve Beagle dogs with 4 months of age were divided into four groups of each three dogs. The first group of the dogs was administered with physiological saline as a control group, while three groups of the dogs were administered with a carcinogenic substance. As the carcinogenic chemical substance, there was employed aflatoxin, and each dog was orally administered singly with 0.5 mg per kg of the body weight of the testing dog, thereby causing tumor. The dogs were fed with high fat feed (containing 40% of fats). The tumor was observed with supersonic diagnosis device and confirmed by the occurrence of an abnormal high signal image (high echo image). The curing was performed by injecting the agent through a catheter into the site of the tumor, the catheter being introduced from the proper hepatic artery into high-dimensionally branched arteries at the tumor site. Before injection of the agent, a contrast medium was injected and the angiograph of the tumor was taken.

Each dog in the first group as a control was injected with 1 ml of a mixture prepared by admixing 1 ml of physiological saline with 1 ml of the contrast medium through a catheter inserted into the high-dimensionally branched arteries at the tumor site from the proper hepatic artery.

Each dog in the second group was injected with 1 ml of a mixture prepared by admixing 1 ml of the preparation formulation example No. 1 with 1 ml of the contrast medium through a catheter inserted into the high-dimensionally branched arteries at the tumor site from the proper hepatic artery.

In the third group, each dog was injected with 1 ml of a mixture prepared by admixing 1 ml of the preparation formulation example No. 2 with 1 ml of the contrast medium through a catheter inserted into the branched arteries at the tumor site from the proper hepatic artery.

In the fourth group, each dog was injected with 1 ml of a mixture prepared by admixing 1 ml of the preparation formulation example No. 6 with 1 ml of the contrast medium through a catheter inserted into the branched arteries at the tumor site from the proper hepatic artery.

Each dog in the first to fourth groups was subjected once per week (four times for four weeks in total) to abnormal high signal image diagnosis with a supersonic diagnosis device as to determine if such abnormal high signal image (high echo image) contracts or expands. On the final date of investigation in four weeks after administration, a catheter was introduced from the proper hepatic artery into the high-dimensionally branched arteries at the tumor site and the contrast medium was injected through the catheter, thereby allowing the angiography to be carried out in order to check if the angiograph has been disappeared or not. The test results are shown in Table 5 below.

TABLE 5

Tests for Curing Hepatic Tumor in Dogs

| Group | Dog No. | Tumor vessels | Size of Tumor | Curing Effects |
|---|---|---|---|---|
| 1 | 1 | Not changed | Expanded | None |
|   | 2 | " | " | " |
|   | 3 | " | " | " |
| 2 | 1 | Decreased | Contracted | Effective |
|   | 2 | " | " | " |
|   | 3 | " | " | " |
| 3 | 1 | " | " | " |
|   | 2 | " | " | " |
|   | 3 | " | " | " |
| 4 | 1 | Disappeared | " | Remarkably effective |
|   | 2 | " | " | Remarkably effective |
|   | 3 | " | " | Remarkably effective |

The injectable preparations in the solution form according to the present invention can achieve local effects by selectively repairing grumous blood vessels and abnormal newborn blood vessels by allowing it to act upon vascular endotheliocytes and causing coagulation of platelets. Further, the injectable preparations in the solution form according to the present invention can achieve such local effects in a reversible manner by varying the concentrations of the injectable preparations. If the active ingredients of the injectable preparations would be high in concentration, the injectable preparations can produce direct effects due to persistent vascular obstruction. On the other hand, if the active ingredients thereof would be contained in a high concentration, the vascular obstruction becomes so reversible that the blood vessels can be repaired and that the blood flow can be allowed to pass again through the vessels. As described hereinabove, the injectable preparations in the solution form according to the present invention can ensure the effectiveness in accordance with symptoms and sites of affected vessels by changing its concentrations. In addition, the action of the injectable preparations in the solution form can be slowed down, as needed, by lowering its concentrations. Furthermore, the injectable preparation in the solution form according to the present invention can produce the local effects by injecting it in a small amount continually into the aneurysm caused in the brain blood vessels through a catheter and by causing the composition of the injectable preparation in the solution form to be stayed in whirls with the blood in the swollen vascular knobs. These local effects allow the swollen portion of the aneurysm to be made matrical and then to be repaired, thereby producing normal blood vessels. As described hereinabove, the injectable preparations in the solution form according to the present invention are extremely effective for treating and curing the affected abnormal tissues because they can treat and cure the affected abnormal tissues in a non-operative way without surgery merely by injecting the curing preparations according to the present invention into the affected abnormal tissues.

The hemorrhoids of the severe grade are caused by a chronically and persistently abnormal extension of the hemorrhoidal veins, thereby causing internal hemorrhoids to occur at the upper outlet side beyond the odontoid line of the anus and external hemorrhoids to occur at the lower anal side. By injecting it directly into the branched peripheral portions of the arteriae haemorrhoidalis superior governing the hemorrhoids, the injectable preparation in the solution form according to the present invention can harden or fibrillate the hemorrhoids or cause the obstruction of the blood vessels, resulting in the disappearance of the hemorrhoids and eventually the recovery of the hemorrhoids.

As the tumor caused in the liver is plenty of abnormal newborn blood vessels and very active in the blood flow through the arteries, the injectable preparation in the solution form according to the present invention can obstruct the blood vessels of the hepatic tumor and suspend the growth of the hepatic tumor by injecting it directly into the high-dimensionally branched arteries at the hepatic tumor site through a catheter introduced thereinto from the proper hepatic artery. Once the growth of the hepatic tumor was suspended, the hepatic tumor can be allowed to disappear through the hepatic tumor cells resulting in the extremely high effects upon the curing of the affected abnormal tissues caused by the hepatic tumor.

Then, a description will be made of experiments for the cytotoxic action of the compositions for treating the affected tissues according to the present invention.

For the injectable preparations obtained in Example No. 1, a comparative review of the cytotoxic effects was made using the endothelial cells of the venous vessel of the human funiculus (primary culture), the fibroblast of the human normal diploid (primary culture) and the rat muscle blast cells (cell culture). As comparative chemicals, there were employed Paoscle™ (containing phenol as a major active ingredient) as an agent for sclerosing the internal piles and Oldamin™ (containing monoethanol amine oleate as a major active ingredient), Aethoxysklerol™ (containing polidocanol as a major active ingredient) and ethanol (containing ethanol as a major active ingredient) as agents for sclerosing esophageal varix.

The method for determining the death of the cells was based on the trypan blue dyeing method.

EXPERIMENT NO. 1

This experiment was carried out in a manner as will be described hereinafter.

Each kind of the cells was inoculated at the rate of $5 \times 10^3$ cells per dish. A 1:1 mixture of 2% procaine hydrochloride and a test agent which was diluted to a 100-fold or 1,000-fold dilution with a cell culture solution (a 0.5% sodium chloride solution) was prepared. To the inoculant was added the dilution, and the resulting mixture was supplied with a 1:1 mixture of DMEM and HAM F12 and a 10% fetal bovine serum. The test cells were then cultured in 5% $CO_2$ at 37° C.

The resulting culture liquid was digested with trypsin to give a cells floating solution to which an equal amount of the test agent was added. This mixture was allowed to stand for 10 minutes at 37° C. and the equal volume of a 0.3% trypan blue solution was added thereto.

The number of the living cells (not dyed with trypan blue) and the dead cells (dyed with trypan blue) were counted in 15 minutes after addition of the trypan blue solution.

As a control, there was used a 0.9% sodium solution (a solution obtained by adding 5% fetal bovine serum to the cells floating solution used for test).

The test results are shown in Table 6 below.

TABLE 6

RATES OF LIVING CELLS

| TEST AGENTS | RATES OF LIVING CELLS (%) | | |
|---|---|---|---|
| | CELL 1 | CELL 2 | CELL 3 |
| Example 1 | 96.8 | 90.3 | 95.0 |
| PAOSCLE ™ | 79.8 | 89.3 | 87.0 |
| OLDAMIN ™ | 0 | 0 | 0 |
| AETHOXYSKLEROL ™ | 0 | 0 | 0 |
| ETHANOL | 0 | 0 | 0 |
| CONTROL (0.9% NaCl Solution) | 97.0 | 91.7 | 94.0 |

Notes:
CELL 1: Endothelial cells of the venous vessel of the human funiculus (primary culture)
CELL 2: Fibroblast of the human normal diploid (primary culture)
CELL 3: Rat muscle blast cells (cell culture)

As is apparent from the test results as shown in Table 6 above, the 0.9% sodium chloride solution used as the control and Paoscle™ did not cause killing a majority of the cells tested, while Oldamin™, Aethoxysklerol™ and ethanol used as the agent for sclerosing the esophageal varix caused the entire number (100%) of the cells.

Among the living cells used in the above tests, the fibroblast of the human normal diploid was cultured again. More specifically, the living cells were washed and inoculated in a culture medium solution containing the same culture medium as used before, followed by the culture at 37° C. for 24 hours. As a result, it was found that no living cells were counted at all out of the cells exposed to the composition according to the present invention, on the one hand, and that 95% of the cells were found alive and kept growing out of the cells treated with the 0.9% sodium chloride solution and 80% of the cells were alive and kept growing out of the cells treated with Paoscle™, on the other hand.

EXPERIMENT NO. 2

The experiment was carried out in substantially the same manner as in Experiment No. 1 above, with the exception that a 2% xylocaine hydrochloride solution was used for the 1:1 mixture of the test agent added to the liquid cell culture medium in place of the 2% procaine hydrochloride solution. It was found as a result of re-culture that the total number (100%) of the fibroblast of the human normal diploid cultured again were dead.

EXPERIMENT NO. 3

The experiment was carried out in substantially the same manner as in Experiment No. 1 above, with the exception that the test chemical alone was added to the cell culture medium (0.9% sodium chloride solution+5% fetal bovine serum). It was found as a result of re-culture that the total number (100%) of the fibroblast of the human normal diploid cultured again were dead.

EXPERIMENT NO. 4

The experiment was carried out in substantially the same manner as in each of the experiment Nos. 1, 2 and 3 above, with the exception that the re-culture was conducted in a liquid cell culture medium to which no 5% fetal bovine serum was not added. It was found as a result of re-culture that the total number (100%) of the fibroblast of the human normal diploid exposed to the composition according to the present invention were dead, while it was found that no cells were killed by the liquid cell culture medium (0.9% sodium chloride solution) used as the control.

INDUSTRIAL UTILIZATION OF THE INVENTION

The injectable compositions in the solution form according to the present invention are constant and stable in formulation as well as effective for treating the affected tissues of the digestive system, particularly the large intestine and rectum, because the injectable compositions comprising substantially the water-soluble aluminum compound, the chelating agent, tannic acid and sodium hydrogen sulfite are adjusted within a pH range of from pH 1.0 to pH 3.5 in such a manner that tannic acid does not react with the metal ions, such as aluminum ions, derived from the water-soluble aluminum compound and no formation of precipitates are caused.

Further, the injectable compositions in the solution form for treating and curing the affected tissues according to the present invention can be made more stable in formulation by adding the polyvalent alcohol and/or the saccharide, as needed, to the compositions substantially comprising the water-soluble aluminum compound, the chelating agent, tannic acid and sodium hydrogen sulfite.

In addition, in preparing the injectable compositions in the solution form for treating and curing the affected tissues according to the present invention, tannic acid is prevented from causing precipitating as a result of its reaction with the metal ions, such as aluminum ions, decomposed from the water-soluble aluminum compound, by adding it to a formulation consisting substantially of the water-soluble aluminum compound, the chelating agent and sodium hydrogen sulfite, whereby the stable compositions having the constant formulation can be prepared.

Furthermore, it is noted that the admixture of a first formulation comprising the water-soluble aluminum compound and the chelating agent with a second formulation comprising tannic acid and sodium hydrogen sulfite can lead to the preparation of the injectable compositions in the solution form according to the present invention, which can offer the advantages in preparing the injectable compositions in the solution form for treating and curing the affected tissues according to the present invention that the reaction of tannic acid with the metal ions such as aluminum ions decomposed from the water-soluble aluminum compound can be controlled more readily so as to cause no precipitating.

It is further advantageous that the optional addition of the polyvalent alcohol and/or the saccharide to the compositions consisting substantially of the water-soluble aluminum compound, the chelating agent, tannic acid and sodium hydrogen sulfite can contribute greatly to making the compositions more stable and preparing the compositions in a ready way because the timing of the addition can be chosen in an optional way.

Furthermore, in preparing the injectable compositions in the solution form in accordance with the method according to the present invention, it is extremely advantageous to enable the pH range of the compositions for treating the affected tissues to be adjusted at an appropriate stage of formulation of each of the components, particularly in terms of making it easy to prevent the oxidation of tannic acid and making it to prevent tannic acid from being reacted with the metal ions derived from the water-soluble aluminum compound.

The present invention can offer the further advantage that the compositions according to the present invention can be made stable in formulation by formulating each of the components at an appropriate stage under atmosphere of inert gases.

Likewise, it is beneficial in preparing the stable injectable compositions in the solution form for treating the affected tissues in accordance with the present invention having the constant and stable formulation that each of the components is formulated under the condition under which no substantial amount or an extremely limited amount of oxygen exists in an atmosphere or in a liquid state because the such condition can contribute particularly to a prevention of the oxidation of tannic acid.

In addition, it is very beneficial in preparing the stable injectable compositions in the solution form for treating and curing the affected abnormal tissues according to the present invention having the constant formulation that a solution containing the polyvalent alcohol and/or the saccharide can be added to or mixed with the first formulation comprising the water-soluble aluminum compound and the chelating agent and/or the second formulation comprising tannic acid and sodium hydrogen sulfite or a mixture of the first formulation with the second formulation immediately before administration, because this way of preparing the injectable preparations in the solution form can prevent each of the components from being changed or transformed according to a lapse of time.

The injectable compositions in the solution form according to the present invention can offer the further advantage that the injectable preparations in the solution form can be stored in a stable state for a long period of time because it is possible to adjust the pH range of the compositions after all the components have been formulated. In addition, it is beneficial for stabilizing the injectable compositions in the solution form for a long period of time that they can be stored under atmosphere of inert gases.

In addition, the injectable preparations in the solution form according to the present invention can demonstrate the excellent curing effects upon the affected abnormal tissues, in particular by repairing the affected abnormal tissues caused by the brain aneurysm, piles or hemorrhoids, hepatic tumor vessels and the like and causing the newborn abnormal vessels to disappear.

What is claimed is:

1. A composition comprising a water-soluble aluminum compound, a chelating agent, tannic acid and sodium hydrogen sulfite, said water-soluble aluminum being contained in a concentration ranging from 0.01 mole to 0.5 mole, said tannic acid being contained at a rate of 0.01% to 25.0% with respect to said water-soluble aluminum compound, said chelating agent being contained at a rate of from 10% to 80% with respect to said water-soluble aluminum compound, and said sodium hydrogen sulfite being contained at a rate of from 50% to 200% with respect to the amount of said tannic acid, wherein a pH of said composition ranges from pH 1.0 to pH 3.5.

2. A composition as claimed in claim 1, further comprising a polyvalent alcohol or a saccharide.

3. A composition as claimed in claim 2, wherein said polyvalent alcohol or said saccharide is mannitol, fructose, xylitol, glucose, galactose, mannose, lactose or glycerin.

4. A composition as claimed in claim 2, wherein said polyvalent alcohol or said saccharide is contained at a rate of from 3% to 20%.

5. A composition as claimed in claim 1, wherein said water-soluble aluminum compound is aluminum chloride, aluminum sulfate, aluminum carbonate aluminum acetate, aluminum nitrate, aluminum lactate, aluminum tartrate, aluminum salicylate, aluminum sodium sulfate, aluminum potassium sulfate, aluminum cesium sulfate or aluminum ammonium sulfate.

6. A composition as claimed in claim 1, wherein said water-soluble aluminum compound is contained at a rate of from 0.03 mole to 0.3 mole.

7. A composition as claimed in claim 1, wherein said water-soluble aluminum compound is contained at a rate of from 1% to 10% as an effective concentration in said composition.

8. A composition as claimed in claim 1, wherein said tannic acid is contained at a rate of from 0.01% to 10.0% as an effective concentration in said composition.

9. A composition as claimed in claim 8, wherein said tannic acid is contained at a rate of from 0.01% to 2.0% as an effective concentration in said composition.

10. A composition as claimed in claim 8, wherein said tannic acid is contained at a rate of from 0.05% to 10.0% as an effective concentration in said composition.

11. A composition as claimed in claim 1, wherein said tannic acid is contained at a rate of from 1% to 20% with respect to said water-soluble aluminum compound.

12. A composition as claimed in claim 1, wherein said chelating agent is citric acid or a salt thereof.

13. A composition as claimed in claim 1, wherein said chelating agent is contained at a rate of from 10% to 80% with respect to the amount of said water-soluble aluminum compound.

14. A composition as claimed in claim 1, wherein said chelating agent is contained at a rate of from 0.1% to 5%.

15. A composition as claimed in claim 1, wherein said sodium hydrogen sulfite is contained at a rate of 0.05% to 0.5%.

16. A composition as claimed in claim 15, wherein said sodium hydrogen sulfite is contained at a rate of 0.1% to 0.3%.

17. A composition as claimed in claim 1, wherein said sodium hydrogen sulfite is contained at a rate of from 70% to 150% with respect to the amount of said tannic acid.

18. A composition as claimed in claim 1, wherein said pH range is set to be from pH 2.0 to pH 3.0.

19. A method for the preparation of a composition comprising a water-soluble aluminum compound, a chelating agent, tannic acid, and sodium hydrogen sulfite as well as having a pH range of from pH 1 to pH 3.5, wherein tannic acid is mixed with a mixture prepared by formulating said water-soluble aluminum compound, said chelating agent, and said sodium hydrogen sulfite in any desired order.

20. A method for the preparation of the composition as claimed in claim 19, wherein a polyvalent alcohol or a saccharide is further contained in the composition.

21. A method for the preparation of the composition as claimed in claim 19, wherein each of the components constituting said composition is formulated under an inert atmosphere.

22. A method for the preparation of the composition as claimed in claim 19, wherein said composition is filled under an inert atmosphere in a container for injection or a container for storing said composition.

23. A method for the preparation of the composition as claimed in claim 19, wherein a pH range of said composition is from pH 2.0 to pH 3.0.

24. A method for the preparation of the composition as claimed in claim 19, wherein said composition is adjusted as needed to said pH range after all of said components constituting said composition have been formulated.

25. A method for the preparation of the composition as claimed in claim 19, wherein oxygen exists in atmosphere or in water to be used in no substantial amount or at such a restricted amount as failing to adversely affect said composition.

26. A method for the preparation of a composition as claimed in claim 19, wherein said composition comprises a water-soluble aluminum compound, a chelating agent, tannic acid and sodium hydrogen sulfite, said water-soluble aluminum being contained in a concentration ranging from 0.01 mole to 0.5 mole, said tannic acid being contained at a rate of 0.01% to 25.0% with respect to said water-soluble aluminum compound, said chelating agent being contained at a rate of from 10% to 80% with respect to said water-soluble aluminum compound, and sodium hydrogen sulfite being contained at a rate of from 50% to 200% with respect to the amount of said tannic acid, wherein a pH of said composition ranges from pH 1.0 to pH 3.5.

27. A method for the preparation of a composition comprising a water-soluble aluminum compound, a chelating agent, tannic acid and sodium hydrogen sulfite as well as having a pH range of from pH 1 to pH 3.5, wherein tannic acid and sodium hydrogen sulfite or a mixture of said tannic acid with said sodium hydrogen sulfite are or is mixed with a mixture prepared by formulating said water-soluble aluminum compound with said chelating agent.

28. A method for the preparation of a composition comprising a water-soluble aluminum compound, a chelating agent, tannic acid and sodium hydrogen sulfite, as well as having a pH range of from pH 1 to pH 3.5;

wherein a first formulation is yielded by mixing said water-soluble aluminum compound with said chelating agent;

wherein separately from said first formulation, a second formulation is yielded by mixing tannic acid with sodium hydrogen sulfite; and wherein said first formulations is mixed with said second formulation.

29. A method for the preparation of the composition as claimed in claim 28, wherein each of said first and second formulations or either one of said first and second formulation or a mixture of the first and second formulations is adjusted, as needed, to said pH range.

30. A method for treating a disease caused by affected tissues of the digestive system comprising orally applying a composition to kill cells of the affected tissues, said composition comprising a water-soluble aluminum compound, a chelating agent, tannic acid, and sodium hydrogen sulfite and having a polyvalent alcohol and/or a saccharide added as needed thereto as well as having a pH range of from pH 1.0 to pH 3.5.

31. A method as claimed in claim 30, wherein said affected tissues comprise piles, hemorrhoids, a brain aneurysm or a hepatic tumor.

32. A method for treating a disease as claimed in claim 30, wherein said composition comprises a water-soluble aluminum compound, a chelating agent, tannic acid and sodium hydrogen sulfite, said water-soluble aluminum being contained in a concentration ranging from 0.01 mole to 0.5 mole, said tannic acid being contained at a rate of 0.01% to 25.0% with respect to said water-soluble aluminum compound, said chelating agent being contained at a rate of from 10% to 80% with respect to said water-soluble aluminum compound, and sodium hydrogen sulfite being contained at a rate of from 50% to 200% with respect to the amount of said tannic acid, wherein a pH of said composition ranges from pH 1.0 to pH 3.5.

33. A method for treating a disease caused by affected tissues of the digestive system comprising injecting a composition to kill cells of the affected tissues, said composition comprising a water-soluble aluminum compound, a chelating agent, tannic acid and sodium hydrogen sulfite and having a polyvalent alcohol and/or a saccharide added as needed thereto, as well as having a pH range of from pH 1.0 to pH 3.5.

34. A composition consisting essentially of a water-soluble aluminum compound, a chelating agent, tannic acid and sodium hydrogen sulfite, said water-soluble aluminum being contained in a concentration ranging from 0.01 mole to 0.5 mole, said tannic acid being contained at a rate of 0.01% to 25.0% with respect to said water-soluble aluminum compound, said chelating agent being contained at a rate of from 10% to 80% with respect to said water-soluble aluminum compound, and sodium hydrogen sulfite being contained at a rate of from 50% to 200% with respect to the amount of said tannic acid, wherein a pH of said comparison ranges from pH 1.0 to pH 3.5.

* * * * *